US006183731B1

(12) United States Patent
Carey et al.

(10) Patent No.: US 6,183,731 B1
(45) Date of Patent: Feb. 6, 2001

(54) METHOD OF REDUCING OR PREVENTING MALODOUR

(75) Inventors: John Carey, Vlaardingen (NL); Jayne Elizabeth Ellis; Corrine Jane Austin, both of Bedford (GB)

(73) Assignee: Unilever Home & Personal Care USA division of Conopco, Inc., Chicago, IL (US)

(*) Notice: Under 35 U.S.C. 154(b), the term of this patent shall be extended for 0 days.

(21) Appl. No.: 09/348,608

(22) Filed: Jul. 6, 1999

(30) Foreign Application Priority Data

Jul. 7, 1998 (GB) .................................... 9814733

(51) Int. Cl.[7] .............................. A61K 7/32; A61K 7/00
(52) U.S. Cl. .......................... 424/65; 424/400; 424/401
(58) Field of Search .............................. 424/65, 400, 401

(56) References Cited

U.S. PATENT DOCUMENTS

| 4,089,942 | 5/1978 | Bore' et al. | 424/47 |
| 5,433,943 | 7/1995 | Osipow et al. | 424/65 |
| 5,512,555 | 4/1996 | Waldstreicher | 514/168 |
| 5,683,682 | 11/1997 | Betts | 424/65 |

FOREIGN PATENT DOCUMENTS

| 19740879 | 4/1999 | (DE) . |
| 0279010 | 8/1988 | (EP) . |
| 2756740 | 6/1998 | (FR) . |
| 2334445 | 8/1999 | (GB) . |
| 94/07837 | 4/1994 | (WO) . |
| 98/063478 | 2/1998 | (WO) . |

OTHER PUBLICATIONS

International Search Report Application No. PCT/GB 99/02153 mailed Nov. 12, 1999.
Fellahi Y et al.: "Synthesis and Antibacterial Activity of 2–substituted 5–(1,2–Diarylethyl)–4,6–Dichloropyrimidine Derivatives" European Journal of Medicinal Chemistry, vol. 30, No. 7, Jan. 1, 1995, pp. 633–639.
Tue, et al.: "Characterisation of Aixilary Aerobic Coryneforms", British Journal of Dermatology, vol. 134, No. 3, 1996, p. 586–XP002120753.
Copending application: Applicant: Casey et al., Serial No.: 09/348,606, Filed: Jul. 6, 1999, For: Cosmetic Composition.
Copending application: Applicant: Casey et al., Serial No.: 09/348,607, Filed: Jul. 6, 1999, For: Method of Reducing or Preventing Malodour.
Copending application: Applicant: Casey et al., Serial No.: 09/348,609, Filed: Jul. 6, 1999, For: Method of Reducing or Preventing Malodour.

*Primary Examiner*—Shelley A. Dodson
(74) *Attorney, Agent, or Firm*—Matthew Boxer

(57) ABSTRACT

Cosmetic method for reducing or preventing body malodor by topically applying to human skin an active agent capable of sub-lethally reducing the bacterial production of odoriferous steroids, characterized in that the agent is an inhibitor of bacterial 4-ene reductase and/or 5α-reductase.

6 Claims, 2 Drawing Sheets

METHOD OF REDUCING OR PREVENTING MALODOUR

Figure 1:
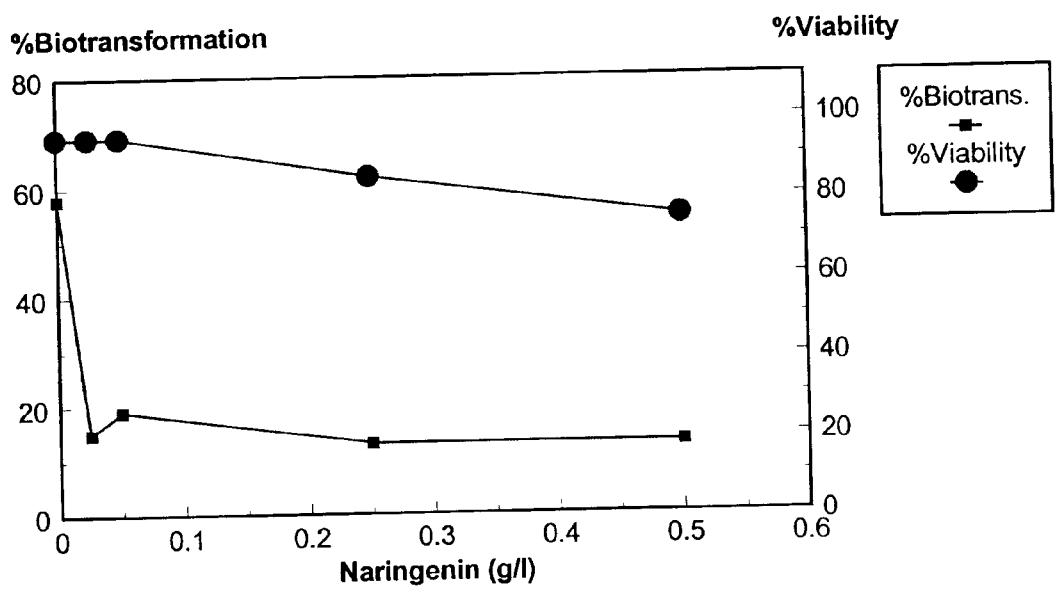

This invention relates to a cosmetic method for reducing or preventing body malodour.

In particular, it relates to a cosmetic method for reducing or preventing body malodour by topically applying to human skin an active agent capable of sub-lethally reducing the bacterial production of odoriferous steroids, characterised in that the agent is an inhibitor of bacterial 4-ene reductase and/or 5α-reductase.

It is well known that freshly secreted sweat is sterile and that body malodour is the result of biotransformation of the sweat by micro-organisms living on the surface of the skin to produce volatile odoriferous compounds.

There are three types of composition routinely used to combat body malodour: perfumes, antiperspirants and deodorants.

Perfumes are designed simply to mask body malodour.

Antiperspirant actives work by blocking the sweat glands thereby reducing perspiration. However, even the best cosmetically acceptable antiperspirant actives rarely reduce sweat production by more than 50%.

Deodorant actives, on the other hand, are designed to reduce the population of micro-organisms living on the surface of the skin. Typical deodorants include ethanol and triclosan (2,4,4'-trichloro,2'-hydroxy-diphenyl ether) which is a well known antimicrobial agent.

The use of common deodorant actives will indiscriminately kill most of the skin's natural microflora to exert a deodorising effect. This indiscriminate action is thought to be a disadvantage of common deodorant products.

Gower et al. (J Steroid Biochem Molec Biol, (1994) Vol. 48, No. 4, pp 409–418) discloses the importance of certain bacterial enzymes involved in bacterial steroid metabolism in the production of odoriferous steroids.

Chen et al. (Dermatology, (1996) Vol. 193, pp 177–184) describes the importance of mammalian 5α-reductase in seborrhoea, acne, female hirsutism and androgenic alopecia. It also discusses the potential use of 5α-reductase inhibitors, in particular finasteride and turosteride in treatment of the above conditions.

Liao et al. (Biochemical and Biophysical Research Communications, (1995) Vol. 214, No. 3, pp 833–838) describes the selective inhibition of mammalian steroid 5α-reductase.

Russell and Wilson (Annual Review of Biochemistry, (1994) Vol. 63, pp 25–61) describes the moderate efficacy of polyunsaturated fatty acids in inhibiting the mammalian 5α-reductase enzymes. In particular it compares the ability of polyunsaturated fatty acids to inhibit these enzymes along with the inability of their mono-unsaturated and saturated counterparts.

U.S. Pat. No. 5 643 559 (Colgate-Palmolive Company) discloses deodorant active materials having an effective amount of Zn++ ions for inhibiting bacterial exoenzymes responsible for the production of axillary malodour. The bacterial exoenzymes are further characterised as aryl sulphatase or beta-glucuronidase.

DE 43 43 265 (Henkel) describes deodorant compositions comprising saturated dioic acid (C3–C10) esters. The active inhibits a sweat decomposing esterase and the compositions are said to not disturb the skin's natural microflora.

WO 94/07837 (Unichema) describes certain novel unsaturated dioic acids having between 8 and 22 carbon atoms. The potential use of these acids to treat malodour is also described.

We have surprisingly found that the bacterial production of odoriferous steroids can be reduced or eliminated without significantly disturbing the skin's natural microflora by sub-lethally inhibiting bacterial enzymes responsible for the production of odoriferous steroids, in particular the 16-androstenes.

We have also found that many inhibitors of mammalian 5α-reductase, e.g. finasteride, are incapable of sub-lethally inhibiting the bacterial production of odoriferous steroids according to the invention.

Accordingly, the invention provides a cosmetic method for reducing or preventing body malodour by topically applying to human skin an active agent capable of sub-lethally reducing the bacterial production of odoriferous steroids, characterised in that the agent is an inhibitor of bacterial 4-ene reductase and/or 5α-reductase.

According to the invention odoriferous steroids include the products or intermediates of bacterial steroid metabolism, in particular the 16-androstenes.

By sub-lethal is meant that cell viability is maintained at 70% or higher, preferably at least 80% and especially at least 90% in a test method according to Example 1 herein. Preferably the bacterial production of odoriferous steroids is reduced by at least 50%, preferably by at least 70% and especially by at least 80% in a test method according to Example 1.

The following contributes an inexhaustive list of active agents employable in a method according to the invention:

dicarboxylic acids, especially unsaturated dicarboxylic acids, e.g. C18:1 dioic acid, and C18:2 dioic acid;

phenyl compounds including:
  phenyl alcohols, e.g. benzyl alcohol, 2-hydroxybenzyl alcohol, 2,3-dimethoxybenzyl alcohol, t-butylhydroquinone, pyrocatechol, and 2-amino-4-nitrophenol;
  phenyl acids, e.g. gallic acid, benzoic acid, salicylic acid and ferulic acid;
  phenyl esters, e.g. benzyl cinnamate;

monoterpene derivatives, e.g. geranic acid;

sterols, e.g. cholesterol, and ergosterol;

steroids, e.g. testosterone, and androstenedione;

flavonoids, e.g. naringenin, isosakuranetin, eriodictyol, and genistein;

steryl esters, e.g. amyrin cinnamate; and 2,7-naphthalenediol, and oxyquinoline.

Mixtures of any two or more of the foregoing actives.

It should be noted that active agents according to the invention do not include perfume components.

By perfume component is meant an ingredient which is added to a perfume to contribute to the olfactory properties of the perfume.

By perfume is meant a mixture of perfume components, and optionally a suitable diluent, which is added to a product to provide it with a pleasing fragrance.

The active agent according to the present invention may preferably be employed in a composition which may be applied to human skin for the reduction or elimination of body malodour. Examples of products comprising an active agent according to the invention include antiperspirants, deodorants, shampoos, conditioners, skin cleansers, detergents, hair conditioners, sunscreens, sun tan lotions, skin conditioners, etc. It is to be understood that this list is not exhaustive with regard to suitable products comprising active agents according to the invention.

Typical deodorant compositions comprising an active agent according to the invention may also comprise other materials commonly found in underarm compositions such as deodorant or antiperspirant compositions, for example, cosmetically acceptable vehicles; deodorant actives; perfumes; antiperspirant actives; skin benefit agents; colours; water; humectants and other cosmetic adjuncts conventionally employed in such compositions. The use of such substances depends on the form of the composition which may be an aerosol, stick, roll-on, gel, lotion, cream, ointment, powder, suspension or soap.

Usually the active agent may be present in an amount ranging from 0.001 to 10% by weight of the composition, preferable from 0.01 to 2%.

In a further embodiment the invention also provides for the use of an active agent according to the invention for reducing or eliminating body malodour.

Furthermore, the invention provides for the use of an active agent according to the invention in the manufacture of a cosmetic composition for reducing or eliminating malodour.

EXAMPLE 1

The ability of inhibitors to inactivate the bacterial 4-ene reductase enzyme was determined in vitro using the conditions given below:

The experiments were carried out in 7 ml glass screw-capped vials containing a suspension (1 ml) of Corynebacterium sp. (NCIMB 40930). This was prepared from a 24 h culture of bacteria grown in growth medium, washed in potassium phosphate buffer (50 mM, pH 6.0), and resuspended in biotransformation medium, as described below. Active-emulsion and substrate (androstadienone 50 μg/assay) were added to the bacterial suspension and experimental samples incubated over 24 h at 35° C. with agitation (100 rpm). Biotransformation of androstadienone to androstenone was measured by capillary GC-MS analysis of the cultures following solvent extraction (Folch et al., J. Biol. Chem. 226: 498–509) with an internal standard, androsterone. Enzyme inactivation of bacterial 4-ene reductase was measured by capillary GC-MS using a Hewlett Packard 5972 MSD GC-MS fitted with a 30 m×0.32 mm HP-5 fused silica capillary column (0.25 μm film thickness) and helium carrier gas. The injection temperature was 80° C., which was held for 1 min, then increased to 200° C. at 10° C./min, then to 300° C. at 20° C./min, with a final holding time of 10 min. Androstenone was identified from fragmentation patterns and standards, and levels in the biotransformation samples were determined using the internal standard and calibration curves of androstenone.

Growth medium used for the preparation of the bacterial inoculum consisted of 200 ml of Tryptone soya broth (20 g/l) (Merck), yeast extract (10 g/l) (Beta Lab), and Tween 80 (2.5 g/l) (Tween is a trade mark of ICI Speciality Chemicals). Biotransformation was carried out in the medium published previously (Kawahara, F. S. (1969) Meths. Enzymol. V, 527–532). The active emulsion was prepared using potassium phosphate buffer (50 mM, pH 6.0), supplemented with Triton X-100 (trade mark of Union Carbide) (5 g/l). This was homogenized to generate an emulsion. Viability of the bacterial cultures was assessed by vital staining using the LIVE/DEAD BacLight® viability kit (Molecular Probes, L-7012).

Figure 2:
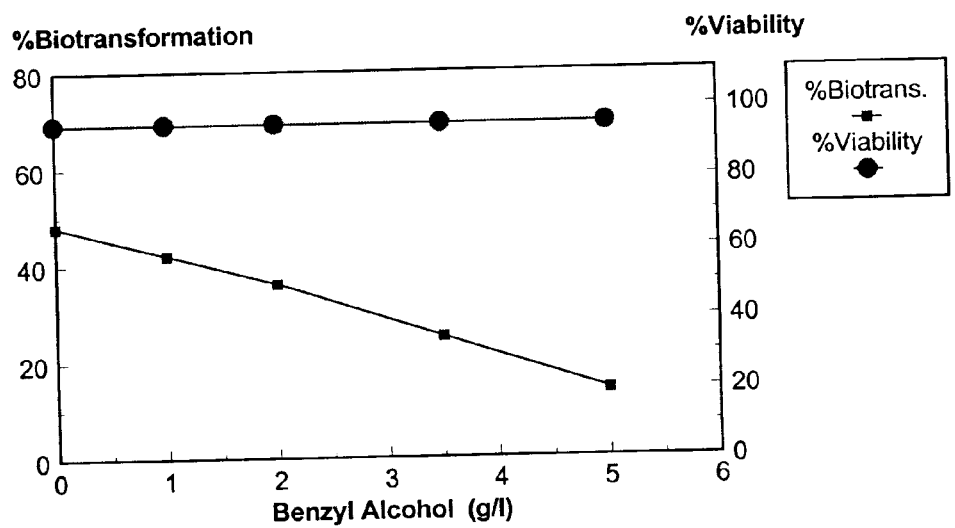
Figure 3:
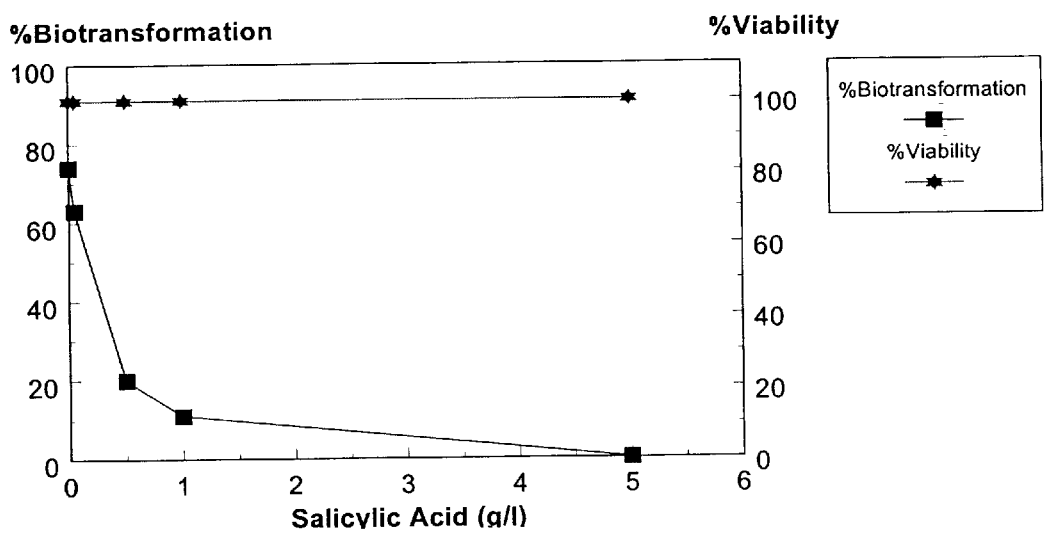

The inactivation of bacterial steroid biotransformation using naringenin, benzyl alcohol and salicylic acid is summarised in Table 1 below, and presented in FIGS. 1 to 3.

By % Biotransformation (FIGS. 1–3) is meant percentage conversion of substrate (androstadienone, 50 μg/assay) to product (androstenone) using the method outlined in Example 1.

TABLE 1

| Active, g/l | Viability (%) | Androstadienone biotransformation (%) | Inhibition of biotransformation (%) |
|---|---|---|---|
| Naringenin | | | |
| 0.0 | 95 | 58 | 0 |
| 0.025 | 95 | 15 | 74 |
| 0.05 | 95 | 19 | 67 |
| 0.25 | 85 | 13 | 78 |
| 0.5 | 75 | 13 | 78 |
| Benzyl alcohol | | | |
| 0.0 | 95 | 48 | 0 |
| 1.0 | 95 | 42 | 13 |
| 2.0 | 95 | 36 | 25 |
| 3.5 | 95 | 25 | 48 |
| 5.0 | 95 | 14 | 71 |
| Salicylic acid | | | |
| 0.0 | 100 | 74 | 0 |
| 0.1 | 100 | 63 | 15 |
| 0.5 | 100 | 20 | 73 |
| 1.0 | 100 | 11 | 85 |
| 5.0 | 100 | 0 | 100 |

EXAMPLE 2

The following is a typical formulation which comprises an active according to the invention.

It is made by methods common in the art.

| Ingredient | Content % by weight |
|---|---|
| Ethanol | 56.5 |
| Benzyl alcohol | 1.00 |
| Isopropyl myristate | 1.0 |
| Fragrance | 1.5 |
| Propellant | 40.0 |

What is claimed is:

1. Cosmetic method for reducing or preventing body malodour by topically applying to human skin an active agent capable of sub-lethally reducing the bacterial production of odoriferous steroids, wherein the agent is an inhibitor of bacterial 4-ene reductase and/or 5α-reductase.

2. Cosmetic method according to claim 1, wherein the odoriferous steroids are 16-androstenes.

3. Cosmetic method according to any one preceding claim, wherein the active agent is an unsaturated dicarboxylic acid.

4. Cosmetic method according to any one preceding claim, wherein the active agent is a flavonoid.

5. Cosmetic method according to any one preceding claim, wherein the active agent is a phenyl derivative.

6. Cosmetic method according to claim 1 or 2, wherein the active agent is selected from the group consisting of naringenin, isosakuranetin, benzyl alcohol, 2-hydroxybenzyl alcohol, C18:1 dioic acid, salicylic acid and mixtures thereof.

* * * * *

UNITED STATES PATENT AND TRADEMARK OFFICE
CERTIFICATE OF CORRECTION

PATENT NO.    : 6,183,731 B1
DATED         : February 6, 2001
INVENTOR(S)   : John Casey, Jayne Elizabeth Ellis and Corrine Jane Austin It is certified that error appears in the above-identified patent and that said Letters Patent is hereby corrected as shown below:

<u>Title page,</u>
Item [12], delete "Carey et al." and insert therefor -- Casey et al. --.
Item [75], Inventors, delete "John Carey" and insert therefor, -- John Casey --.

Signed and Sealed this

Fifteenth Day of April, 2003

JAMES E. ROGAN
*Director of the United States Patent and Trademark Office*